(12) United States Patent
Tomat et al.

(10) Patent No.: US 9,486,423 B2
(45) Date of Patent: Nov. 8, 2016

(54) REDOX-DIRECTED CHELATORS TARGETING INTRACELLULAR METAL IONS

(71) Applicant: THE ARIZONA BOARD OF REGENTS ON BEHALF OF THE UNIVERSITY OF ARIZONA, Tucson, AZ (US)

(72) Inventors: Elisa Tomat, Tucson, AZ (US); Tsuhen Chang, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 14/531,634

(22) Filed: Nov. 3, 2014

(65) Prior Publication Data

US 2015/0126610 A1 May 7, 2015

(51) Int. Cl.
*A61K 31/175* (2006.01)

(52) U.S. Cl.
CPC .................................. *A61K 31/175* (2013.01)

(58) Field of Classification Search
None
See application file for complete search history.

(56) References Cited

PUBLICATIONS

Chang and Tomat. Disulfide/thiol switches in thiosemicarbazone ligands for redox-directed iron chelation. Dalton Trans, Apr. 16, 2013, 42, 7846-7849.*

* cited by examiner

*Primary Examiner* — Anna Pagonakis
(74) *Attorney, Agent, or Firm* — Don D. Cha; Hamilton DeSanctis & Cha, LLP.

(57) ABSTRACT

The present invention provides redox-activated chelators and methods for using the same to treat cancer. In one particular embodiment, the redox-activated chelator is of the formula:

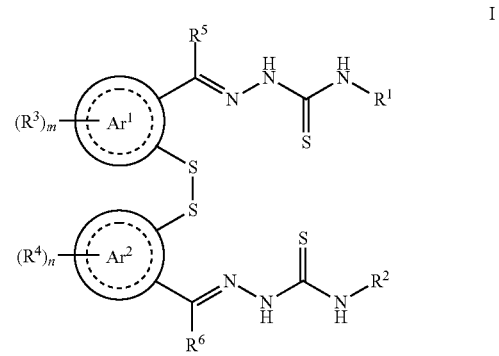

wherein
each of m and n is an integer from 0 to 4;
each of $Ar^1$ and $Ar^2$ is independently aryl or heteroaryl;
each of $R^1$, $R^2$, $R^5$ and $R^6$ is independently hydrogen, alkyl, aryl, electron withdrawing group or an anion stabilizing group;
each of $R^3$ and $R^4$ is independently alkyl, halide, or other electron withdrawing group or an anion stabilizing group.

7 Claims, 6 Drawing Sheets

1a R = H, 1b R = CH$_3$, 1c R = Ph

2a R = H, 2b R = CH$_3$, 2c R = Ph

REDOX-DIRECTED CHELATORS TARGETING INTRACELLULAR METAL IONS

CROSS-REFERENCE TO RELATED APPLICATIONS

This application claims the priority benefit of U.S. Provisional Application No. 61/899,262, filed Nov. 3, 2013, which is incorporated herein by reference in its entirety.

FIELD OF THE INVENTION

The present invention relates to redox-activated chelators and methods for using the same to treat cancer.

BACKGROUND OF THE INVENTION

It is believed that compared to normal cells, cancer cells require higher iron levels in order to sustain fast proliferation rates. Cell walls in various tumor types are characterized by upregulated expression of the transferrin receptor (TfR), which is responsible for increased cellular uptake of the iron transport protein transferrin (Tf). As such, the use of small-molecule scavengers (e.g., chelators) that avidly sequester intracellular iron ions is emerging as a potential therapeutic avenue in cancer research. Iron chelation therapy has been employed commonly and successfully for decades in the clinical treatment of iron overload disorders associated with genetic conditions such as β-thalassemia and hemochromatosis. In the context of cancer chemotherapy, iron chelators such as desferrioxamine (DFO, Desferal®), a clinically approved drug for iron overload treatment, have shown promising antiproliferative activity.

In clinical trials, however, their applicability has been hampered by dose-limiting toxicity and adverse side effects. Chelators derived from bacterial siderophores (e.g., DFO) or other high-affinity scaffolds affect iron levels not only in cancer cells but also in normal tissue and blood plasma in a non-discriminatory fashion. Although suitable for patients battling iron overload, such chelators are not designed to target the higher iron demand of malignant cells in cancer patients presenting normal or low systemic iron levels.

New levels of molecular design are required for chelation-based therapeutics to evolve from their established roles in metal overload treatment. For instance, several pro-chelator approaches are under investigation for the development of multifunctional chelators as therapeutic agents for conditions associated with metal dyshomeostasis, such as neurodegenerative diseases and Wilson's disease.

Because the intracellular environment of tumor cells presents lower (more reducing) potentials when compared to blood plasma and neighboring normal tissue, redox directed chelation therapy could lead to preferential or selective depletion of iron in cancer cells and ultimately tumor-targeted therapeutic avenues.

Therefore, there is a need for pro-chelators that can be activated for iron coordination following a reduction event within cancer cells.

SUMMARY OF THE INVENTION

Some aspects of the invention are based on the discovery by the present inventors of various redox-activated pro-chelator compounds. In particular, one aspect of the invention provides a method for treating a clinical condition associated with a metal dysregulation in a subject in need of such a treatment. As used herein, the term "a clinical condition associated with a metal dysregulation" includes (i) a clinical condition associated with a metal-ion overload such as iron ion-overload; and (ii) a clinical condition that results in or leads to metal dysregulation compared to a normal cell, e.g., cancer. Thus, the term "a clinical condition associated with a metal dysregulation" includes, but is not limited to, clinical conditions (i.e., abnormal conditions, disease, etc.) that is caused by or resulting in metal (e.g., iron) ion-overload in cells and clinical conditions that results in abnormal metal ion-usage (either a significantly more or significantly less) by the cell compared to normal cells.

Such a method typically includes administering to the subject in need of such a treatment a therapeutically effective amount of a redox-activated pro-chelator. The redox-activated pro-chelator is preferentially or selectively reduced within a cell having a metal dysregulation to produce a metal-ion chelating moiety whereby chelation of metal ion by said metal chelating moiety within the cell with a metal dysregulation alleviates said clinical condition associated with the metal dysregulation.

In some embodiments, the metal ion is iron ion.

Yet in other embodiments, said metal ion chelating moiety comprises a thiosemicarbazone moiety.

Still in other embodiments, said redox-activated pro-chelator comprises a disulfide linkage that is configured to be reduced, typically selectively or preferentially, within a cancer cell to produce a thiol compound that is configured to chelate iron ion within the cancer cell. In some instances, said redox-activated pro-chelator is of the formula:

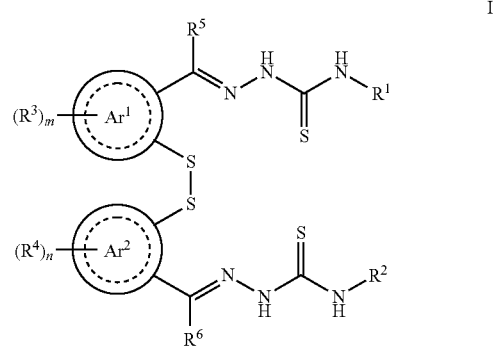

wherein
each of m and n is an integer from 0 to 4;
each of $Ar^1$ and $Ar^2$ is independently aryl or heteroaryl;
each of $R^1$, $R^2$, $R^5$ and $R^6$ is independently hydrogen, alkyl, aryl, electron withdrawing group or an anion stabilizing group;
each of $R^3$ and $R^4$ is independently alkyl, halide, electron withdrawing group or an anion stabilizing group.

Within these instances, in some cases, m and n are 0. In other instances, each of $R^1$ and $R^2$ is independently hydrogen, methyl or phenyl. Still in other instances, said redox-activated pro-chelator is of the formula:

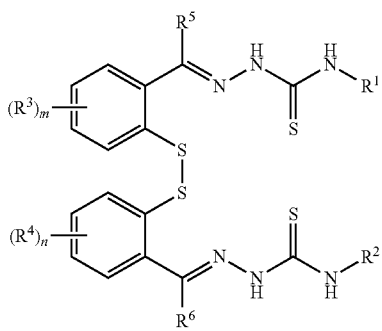
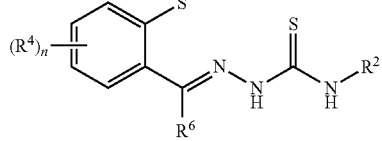

wherein m, n, $R^1$, $R^2$, $R^3$, $R^4$, $R^5$ and $R^6$ are those defined above.

Yet another aspect of the invention provides a method for treating cancer in a subject, said method comprising administering to said subject in need of such a treatment a therapeutically effective amount of a redox-activated pro-chelator that is configured to be reduced, typically preferentially or selectively, within a cancer cell, wherein said redox-activated pro-chelator is of the formula:

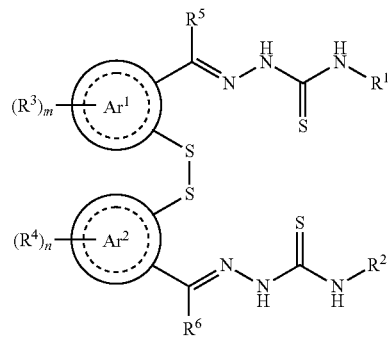

wherein
  each of m and n is an integer from 0 to 4;
  each of $Ar^1$ and $Ar^2$ is independently aryl or heteroaryl;
  each of $R^1$, $R^2$, $R^5$ and $R^6$ is independently hydrogen, alkyl, aryl, electron withdrawing group or an anion stabilizing group;
  each of $R^3$ and $R^4$ is independently alkyl, halide, electron withdrawing group or an anion stabilizing group.

Unless the context requires otherwise, the terms "preferentially" and "selectively", when referring to reduction of a compound of the invention, are used interchangeably herein and means that the compound is more easily reduced in a cancer cell (or any other cell that exhibits a clinical condition due to metal dysregulation) than a normal cell. Typically, the compound of the invention is at least 5%, often at least 10%, and more often at least 25%, more likely to be reduced in a cancer cell than a normal cell. Such a selectivity can be determined, for example, by treating cancer cells and normal cells in vitro under the same experimental conditions with a compound of the invention and comparing the amount of compounds reduced in the normal cell at $T_{1/2}$ of cancer cells, where $T_{1/2}$ represents the time it takes for reduction of ½ the amount of compound in cancer cells.

Still another aspect of the invention provides a method for treating a clinical condition associated with iron ion-dysregulation in a cell, said method comprising administering to a patient in need of such a treatment a redox-activated pro-chelator that is selectively reduced within a cell with iron ion-overload, wherein said redox-activated pro-chelator is of the formula:

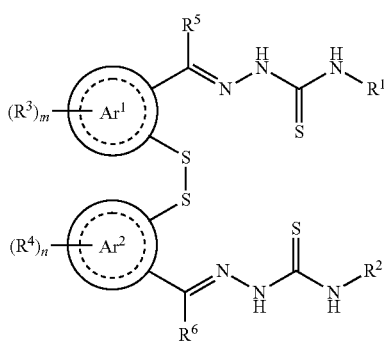

wherein
  each of m and n is an integer from 0 to 4;
  each of $Ar^1$ and $Ar^2$ is independently aryl or heteroaryl;
  each of $R^1$, $R^2$, $R^5$ and $R^6$ is independently hydrogen, alkyl, aryl, electron withdrawing group or an anion stabilizing group;
  each of $R^3$ and $R^4$ is independently alkyl, halide, electron withdrawing group or an anion stabilizing group.

In some embodiments, said clinical condition comprises cancer, a neurodegenerative disorder, hemochromatosis, or thalassemia. In some cases, said clinical condition comprises breast cancer, lung cancer, prostate cancer, leukemia or ovarian cancer.

BRIEF DESCRIPTION OF THE INVENTION

FIG. 1 shows schematic illustration of reduction of a disulfide switch for the activation of a thiosemicarbazone metal ion chelator.

FIG. 2 is a graph showing reduction of $(TC1-S)_2$ (9.0 µM) by GSH (11.0 mM) as monitored by UV-visible absorption spectroscopy in buffered aqueous solution (50 mM PIPES, pH 7.4) at 25° C. Spectral changes during the reduction of $(TC1-S)_2$ (Line 2, 9.0 mM) to TC1-SH (Line 1) by GSH (11.0 mM). The reaction goes to substantial completion within 2 h.

FIG. 3 is a graph showing the fraction of reduced chelator TC1-SH obtained from UV-visible absorption data in GSH/GSSG redox buffer solutions at different half-cell potentials. Total ([GSH]+[GSSG]) was maintained at 11-13 mM, whereas initial [$(TC1-S)_2$] was 12.5 µM. Samples were allowed to equilibrate for 2 h. Data points are plotted as average of triplicate measurements±standard deviation.

FIG. 4 is a bar graph showing the effect of N-acetyl cystein (NAC) supplementation on the toxicity of DFO (10 µM) and $(TC1-S)_2$ (10 µM). MDA-MB-231 cells were incubated with NAC for 6 h before treatment with DFO (10.0 µM) or $(TC1-S)_2$ (10.0 µM) for 48 h. Percent viability is expressed relative to control treated with DMSO and averaged over three experiments±percent standard deviation.

FIG. 5 is a graph showing displacement of paramagnetic ions and restoration of calcein fluorescence by addition of chelators $(TC1-S)_2$ and SIH at the indicated times and final concentrations in suspended Jurkat cell cultures. Fluorescence intensity at 517 nm (excitation, 488 nm) is plotted as the difference from the initial values before any addition. DMSO concentration was kept constant in all solutions.

FIG. 6 is EPR spectra of intact Jurkat cells: (1) untreated cells, (2) after treatment with 50 mM DFO for 3 hours, and (3) after treatment with 50 mM $(TC1-S)_2$ for 1 hour. Experimental conditions: microwave frequency, 9.338 GHz; microwave power, 2 mW; magnetic field modulation amplitude, 0.5 mT; temperature, 30° K.

FIG. 7 is a bar graph showing the effect of TC1-SH and DFO on the extent of benzoate hydroxylation to form fluorescent salicylate(s) (ex: 290 nm, em: 410 nm) in the presence of Fe(II) ions (30 µM) and $H_2O_2$. All solutions were prepared in phosphate buffer (10 mM, pH 7.40) and incubated for 3 h following addition of $H_2O_2$. EDTA (30 µM) was employed as a positive control. Measurements were conducted in triplicate and reported as average±standard deviation.

FIG. 8 is a bar graph showing intracellular generation of ROS monitored through the oxidation of $DCFH_2$ to fluorescent DCF (ex: 485 nm, em: 528 nm). MDA-MB-231 cells were treated with $DCFH_2$-DA (10 µM, 10 min), washed and then incubated with test compounds (concentrations as shown, 30 min). $H_2O_2$ (100 µM) was employed as a positive control. Measurements were conducted in triplicate and reported as average±standard deviation.

Figure 11:
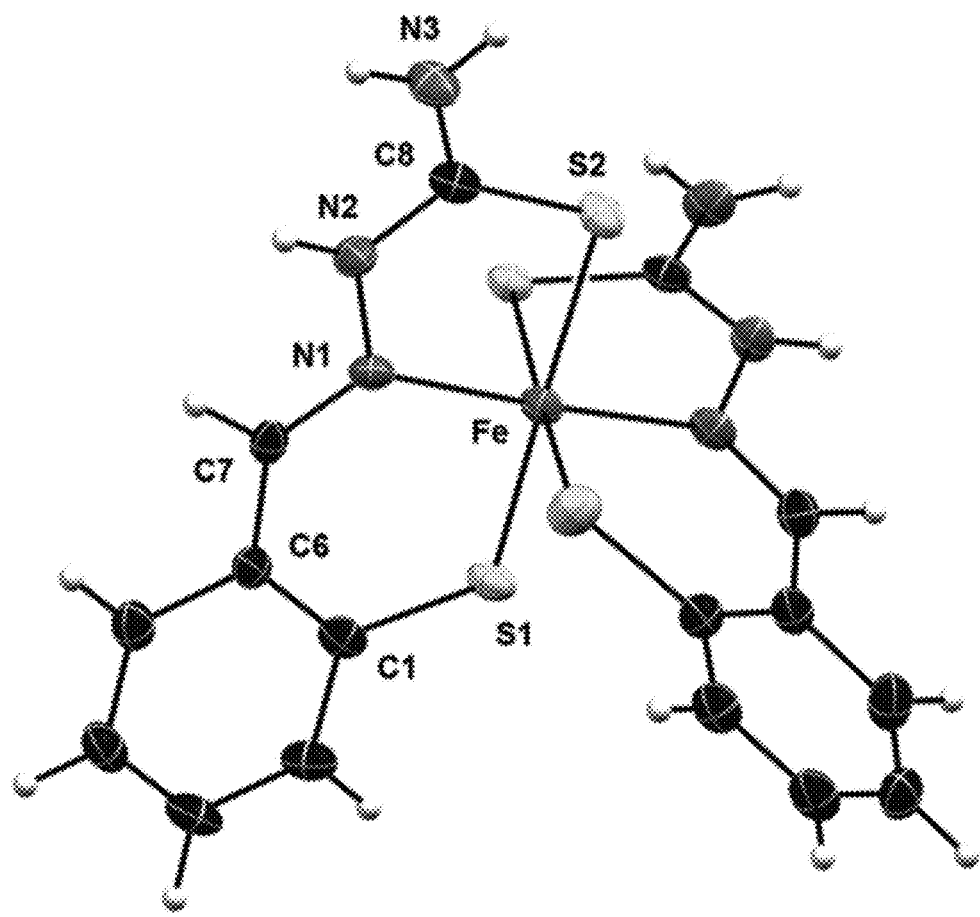

FIG. 11 is a crystal structure of the cation in compound 3a showing a partial labeling scheme. The $BF_4^-$ counterion, as well as two THF molecules, are not shown for clarity. Thermal ellipsoids are scaled to the 50% probability level. CCDC 915453.

DETAILED DESCRIPTION OF THE INVENTION

Definitions

"Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Exemplary alkyl group include, but are not limited to, methyl, ethyl, n-propyl, 2-propyl, tert-butyl, pentyl, and the like.

"Aryl" refers to a monovalent mono-, bi- or tricyclic aromatic hydrocarbon moiety of 6 to 15 ring atoms which is optionally substituted with one or more substituents within the ring structure. When two or more substituents are present in an aryl group, each substituent is independently selected.

The term "heteroaryl" means a monovalent monocyclic or bicyclic aromatic moiety of 5 to 12 ring atoms containing one, two, or three ring heteroatoms selected from N, O, or S, the remaining ring atoms being C. The heteroaryl ring is optionally substituted independently with one or more substituents. Exemplary heteroaryls include, but are not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to a pharmacologically substantially inactive derivative of a parent drug molecule that requires biotransformation, either spontaneous or enzymatic, within the organism to release the active drug. Prodrugs are variations or derivatives of the compounds of this invention, which have groups cleavable under metabolic conditions. Prodrugs become the compounds of the invention which are pharmaceutically active in vivo when they undergo solvolysis or reduction or other reaction eliciting activation under physiological conditions or undergo enzymatic processing. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, *Design of Prodrugs*, pp. 7-9, 21-24, Elsevier, Amsterdam 1985 and Silverman, *The Organic Chemistry of Drug Design and Drug Action*, pp. 352-401, Academic Press, San Diego, Calif., 1992). Prodrugs commonly known in the art include acid derivatives that are well known to one skilled in the art, such as, but not limited to, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. For example, a compound of the invention having free amino, amido, hydroxy or carboxylic groups can be converted into prodrugs. Prodrugs include compounds wherein an amino acid residue, or a polypeptide chain of two or more (e.g., two, three or four) amino acid residues, which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of a compound of the invention through the carbonyl carbon prodrug sidechain.

The term "chelator" refers to a compound or a moiety that is capable of coordinating (or binding) a metal ion in a polydentate (e.g., coordination via two or more atoms of moieties) fashion.

The terms "pro-chelator" and "prochelators" are used interchangeably herein and refer to a compound or a moiety that is transformed into a chelator following activation via a chemical reaction (e.g., with or by another compound including via redox reaction) or by an enzyme.

The term "anion stabilizing group" refers to a moiety whose presence in the molecule increases the stability of the anion relative to the absence of such a group. One skilled in the art can readily determine whether a substituent or a moiety is an anion stabilizing group, e.g., by determining the increase in the acidity of the resulting compound compared to a corresponding compound in the absence of such group. One can empirically determine the anion stabilization of a particular group by determining the pKa of the compound having the anion stabilizing group and comparing it with the pKa of the corresponding compound in the absence of the anion stabilizing group. Typically, the anion stabilizing compound will have a lower pKa, i.e., it will be more acidic.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "iron ion-overload" refers to a cell whose iron ion concentration is above the normal iron ion concentration and manifest abnormal clinical condition. The iron ion-overload can be the cause of the clinical condition or it can be a result of the clinical condition. It should be appreciated that the iron ion concentration of a normal cell can vary depending on the type of cells. The terms "iron overload" and "iron ion-overload" are used interchangeably herein and typically refers to the condition of patients presenting systemic iron concentrations that are significantly higher than normal, e.g., the amount of iron concentration in subjects that do not show any observable clinical condition(s). Iron overload can be due to accidental exposure to excessive iron or to genetic conditions that lead to accumulation of iron, such as hemochromatosis, or to conditions that require multiple blood transfusions, such as thalassemia. Thus, a clinical condition associated with the iron overload includes clinical condition in which the iron ion-overload is a cause or the effect of such a clinical condition.

It is believed that cancer cells do not have a significantly higher systemic iron levels in general. However, cancer cells are more susceptible to iron deprivation because they require higher iron levels. Accordingly, in some embodiments of the invention, the method includes treating a cancer patient by administering a therapeutically effective amount of a compound of the invention. In these embodiments, the amount of compound administered is of sufficient amount to cause deprivation of iron in cancer cells to effectively cause apoptosis of cancer cells.

As used herein, the terms "those defined above" and "those defined herein" when referring to a variable incorporates by reference the broad definition of the variable as well as any narrow and/or preferred, more preferred and most preferred definitions, if any.

DESCRIPTION OF THE INVENTION

The present invention provides compounds, compositions and methods for using or producing such compounds and compositions that are redox-activated for treating a clinical condition associated with a metal dysregulation, e.g., iron overload, in a cell. In particular, compounds of the invention are redox-activated in vivo to treat such a clinical condition. Some of the clinical conditions that can be treated using the invention include, but are not limited to, cancer, neurodegenerative disorders such as Parkinson's disease and Alzheimer's disease, and conditions associated to iron overload such as hemochromatosis and thalassemia. Specific examples of cancers that could be treated by the invention include, but are not limited to, breast cancer, lung cancer, prostate cancer, leukemia, and ovarian cancer.

Compounds of the invention that are redox-activated are also referred to herein as "pro-chelator" or "prochelators." In some embodiments, compounds of the invention are reduced at half-cell potentials between −160 and −220 mV (vs SHE at 25° C.). Alternatively, compounds of the invention are reduced at half-cell potentials of about −150 mV or lower, typically −160 mV or lower, and often −180 mV or lower, and most often about −200 mV or lower. The term "about" refers to ±20%, typically ±10%, and often ±5% of the numeric value. Without being bound by any theory, it is believed that by having such a low redox potential, a significant amount of compounds of the invention are activated within a target cell rather than in blood plasma. For example, it is believed at least 70%, typically at least 80%, and often at least 90% of the compound of the invention, when administered, is activated within the cancer cell.

As discussed above, while any clinical condition that is associated with or exhibited by a metal dysregulation compared to the same normal (i.e., exhibiting no clinical symptoms) cells can be treated by the invention, for the sake of brevity and clarity, the invention will now be described in reference to treating cancer. However, it should be emphasized that one skilled in the art having read the present invention can readily practice the invention to treat other clinical conditions that are associated with a metal dysregulation in a cell. It should also be noted that the metal dysregulation can be the cause and/or the effect of a clinical condition.

A reprogrammed metabolism of iron has recently emerged as a characteristic of malignancy. This notion is supported by epidemiological studies and, at a molecular level, by the altered expression of key handlers of intracellular iron availability, such as transferrin, ferritin and ferroportin, in cancer cells when compared to normal cells. Given its well-established role in cell proliferation, iron is critical for tumor growth. In addition, recent evidence connects this essential nutrient to metastasis and the development of a favorable tumor microenvironment.

Some aspects of the invention are based on the accumulating evidence on the complex relationship between iron and cancer. Such a relationship has lead the present inventors to the preparation and study of small molecules (e.g., chelators) capable of capturing iron ions in biological settings. Such compounds are expected to provide new tools in cancer treatment and determination of prognosis. As discussed above, several iron chelators, such as desferrioxamine (DFO), are commonly employed in the clinic for the treatment of iron overload disorders and have been tested in the context of cancer chemotherapy. In fact, studies have revealed promising antiproliferative behavior of iron chelators in cancer cell cultures and in vivo. The susceptibility of cancer cells to iron deprivation is therefore used by the present inventors as a therapeutic opportunity in cancer chemotherapy.

Prochelation strategies, in which the chelator is activated in response to a triggering event, increase the selectivity of biologically active chelators, and are therefore addressing a contemporary challenge in the design of chelation approaches targeting conditions, such as cancer and neurodegenerative disorders, that are not characterized by systemic metal overload. The thiosemicarbazone moiety characterizes a large number of biologically active metal scavengers. Accordingly, some aspects of the invention are based on the development of a prochelation approach by the present inventors incorporating the redox-directed activation of a thiosemicarbazone. For example, because tumor cells present a more reducing environment when compared to the normal cells, the prochelation strategy disclosed herein can be used to preferentially or selectively activate the chelating system in malignant cells, thereby allowing treatment of cancer with significantly reduced side-effects and/or more efficiently.

Figure 1:
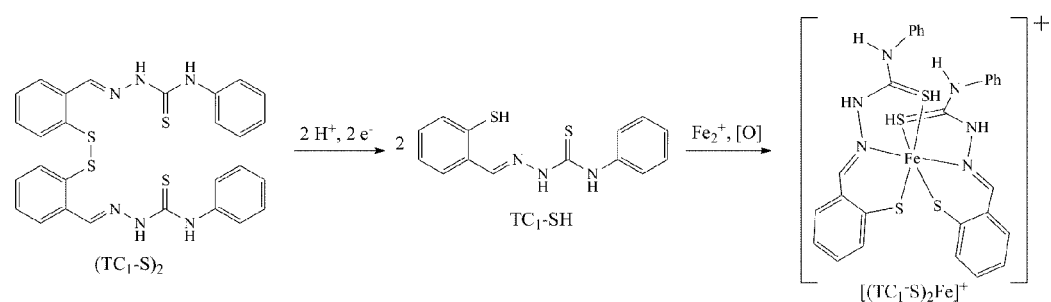

In one particular aspect of the invention, a disulfide bond is used to mask one of the sulphur atoms in the S,N,S donor set of a thiosemicarbazone ligand, to afford a prochelator. See, for example, compound $(TC1-S)_2$ in FIG. 1. The presence of a disulfide bond significantly eliminates or prevents chelation of any metal ions in a relatively non-reducing condition, e.g., in blood plasma. Following reduction, e.g., in a cancer cell, the corresponding thiol TC1-SH readily coordinates iron in what is believed to be a 2:1 ligand-to-metal stoichiometry. FIG. 1. Again without being bound by any theory, it is believed that as observed for DFO and other siderophores, this ligand stabilizes iron in its trivalent oxidation state and therefore coordination of Fe(II) is believed to occur concurrently to oxidation, yielding a stable Fe(III) complex.

The present inventors have discovered that prochelators of the invention, e.g., compound $(TC1-S)_2$ in FIG. 1, exhibit antiproliferative activity in SK-N-MN (neuroepithelioma) and MDA-MB-231 (breast adenocarcinoma) cells with $IC_{50}$ values in the low micromolar range, similar to those associated with antiproliferative chelator DFO. Notably, $(TC1-S)_2$ was significantly less toxic than DFO in normal lung fibroblasts, which are expected to be less susceptible to iron deprivation and to present a less reducing intracellular environment. The present inventors have studied the fate of the prochelator through its reduction/activation and iron coordination in the intracellular environment.

Without being bound by any theory, it is believed that the disulfide bond in $(TC1-S)_2$ functions as a switch in this redox-directed chelation approach because its reduction to the corresponding thiols is required to "switch on" iron sequestration. This activation event is believed to occur in the reducing conditions characterizing the intracellular space, in which the glutathione redox buffer (GSH/GSSG) is present in millimolar concentrations and acts as a major regulator of the intracellular redox environment.

Figure 2:
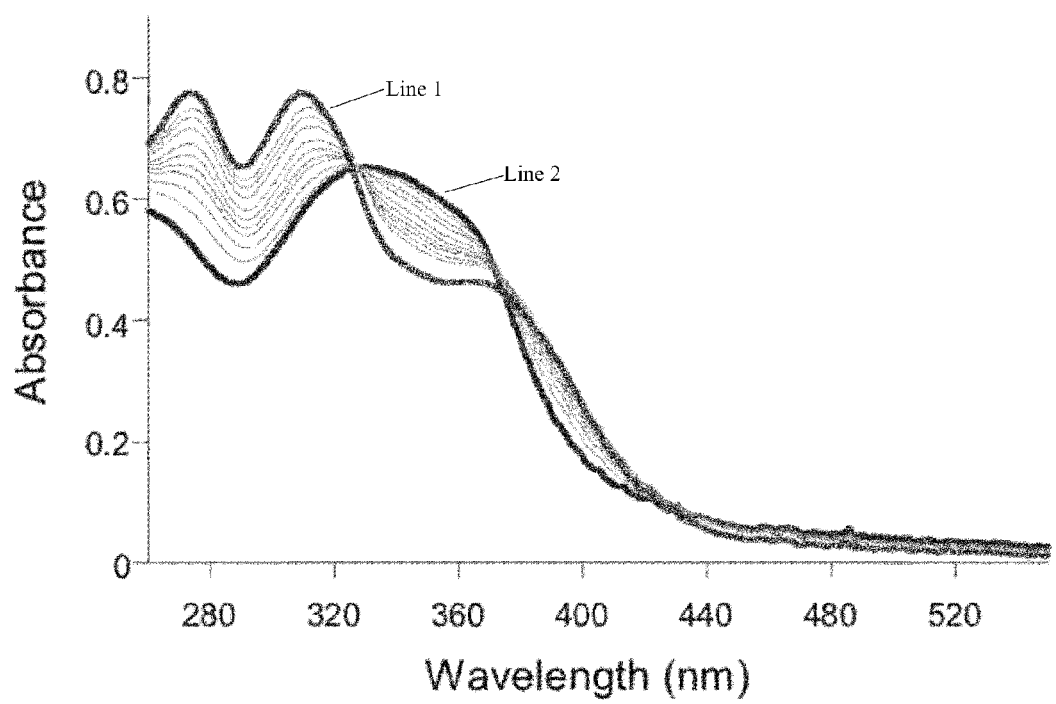

The reduction of $(TC1-S)_2$ can be monitored in vitro by UV-visible absorption spectroscopy. FIG. 2. In the presence of reduced glutathione (GSH, 11.0 mM) in neutral buffered aqueous solution, disulfide $(TC1-S)_2$ (9.0 μM) was converted substantially quantitatively to the thiol RSH (FIG. 2), which was stable in solution for over 6 h (data not shown).

Figure 3:
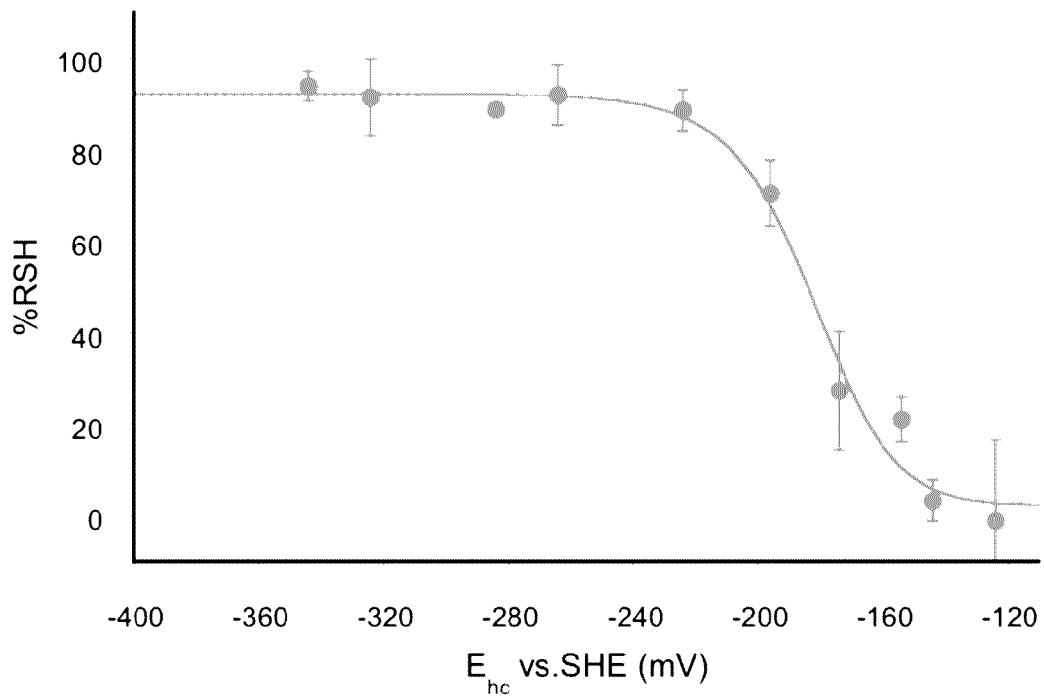

In order to estimate the speciation of the prochelator/chelator system in solutions containing glutathione levels reflecting biologically relevant conditions, disulfide $(TC1-S)_2$ was allowed to equilibrate in a series of redox buffer mixtures. The half-cell potentials for the solutions were calculated based on the concentrations of GSH and GSSG and they were selected to include values from those typically associated to proliferating cells (−240 mV vs SHE) to those found in necrotic cells (−180 mV). Based on the differences in spectral features of $(TC1-S)_2$ and TC1-SH in the 260-400 nm range, the estimated equilibrium percentage of thiol RSH was found to be greater than 80% at half-cell potentials of −220 mV or lower. FIG. 3. As such, in this model of intracellular conditions containing micromolar chelation system and millimolar glutathione buffer, the chelation system after equilibration was found prevalently in its reduced iron-binding form at glutathione half-cell potentials that are characteristic of proliferating and malignant cells.

Figure 4:
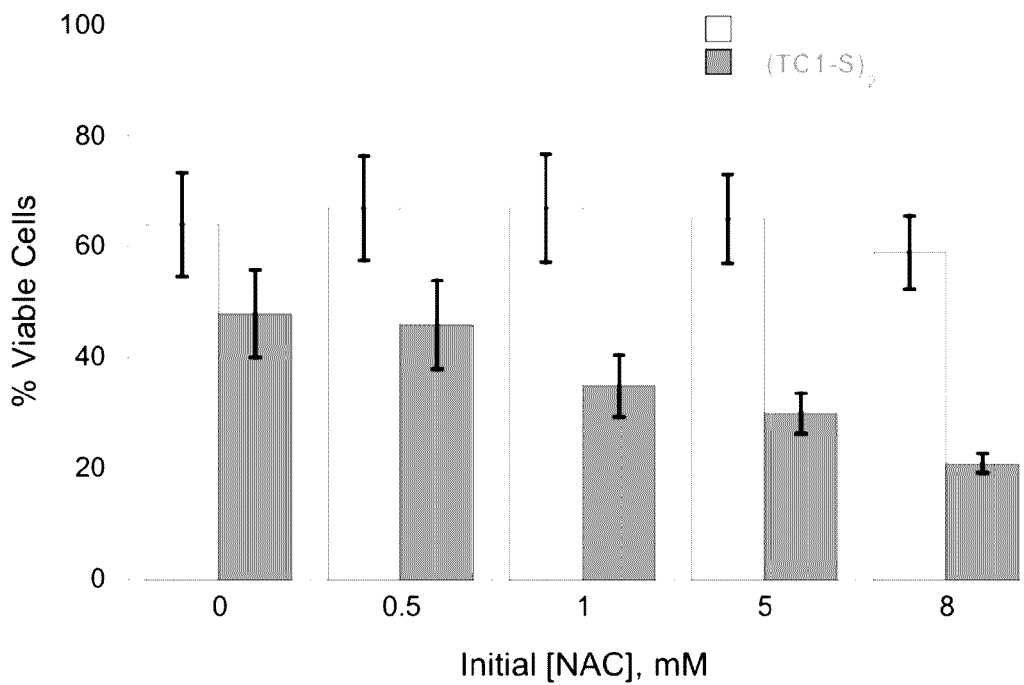

The control of reducing conditions employed in vitro in the experiments summarized above cannot be achieved in cell culture; nevertheless, the intracellular concentration of GSH can be increased by supplementing with N-acetyl cysteine (NAC), a precursor required for GSH biosynthesis. NAC supplementation was expected to lead to increased levels of reduced chelator and hence higher toxicity in cell culture. This effect was indeed observed in breast adenocarcinoma cells (MDA-MD-231), in which (TC1-S)$_2$ was previously found cytotoxic with a 4.6 μM IC$_{50}$ (48 h). In experiments conducted at fixed (TC1-S)$_2$ concentration (10.0 μM), cells were more susceptible to (TC1-S)$_2$ toxicity in the presence of increasing amounts of NAC in viability assays. FIG. 4. Conversely, the antiproliferative siderofore desferrioxamine (DFO, IC$_{50}$ 17.0 μM in MDA-MD 231 cells, 48 h), which does not require a reduction/activation step, was not affected significantly by NAC concentrations in these assays.

These experiments show that the reduction of the disulfide switch in (TC1-S)$_2$ falls in the range of potentials that are relevant to the intracellular concentrations of glutathione redox buffer. The extent of such reduction responds to changes in GSH concentrations (FIG. 3) that are associated to life cycle transitions (for instance, from differentiation to proliferation) and correlates to higher toxicity in more reducing conditions in live cultured cells (FIG. 4). Because rapidly dividing cancer cells typically present higher [GSH]/[GSSG] ratios when compared to the neighboring normal tissue, these findings probing the reduction of (TC1-S)$_2$ are consistent with the preferential activation of the chelation system in more reducing tumour tissue.

Thiol TC1-SH readily coordinates Fe(II) ions in organic and aqueous solutions in a 2:1 ligand-to-metal stoichiometry complex, which is concurrently oxidized to a Fe(III) species in the presence of trace oxygen. This low-spin ferric complex was believed to also form intracellularly upon reduction of disulfide (TC1-S)$_2$ and subsequent iron coordination. The formation of this species in live cultured cells upon exposure to the pro-chelator (TC1-S)$_2$ was confirmed as described below.

Intracellular iron binding was first examined using calcein-AM, the acetoxymethyl ester of a fluorescein-based sensor of metal ions in biological specimens. Trapped intracellularly upon hydrolysis of the ester groups by esterases, calcein coordinates iron and possibly other (far less abundant) cations (e.g., Cu(II) and Zn(II)). Calcein stabilizes ferric iron coordination and this paramagnetic ion quenches considerably its fluorescence emission. Hence, changes in calcein fluorescence intensity have been correlated with variations in intracellular iron concentrations.

Figure 5:
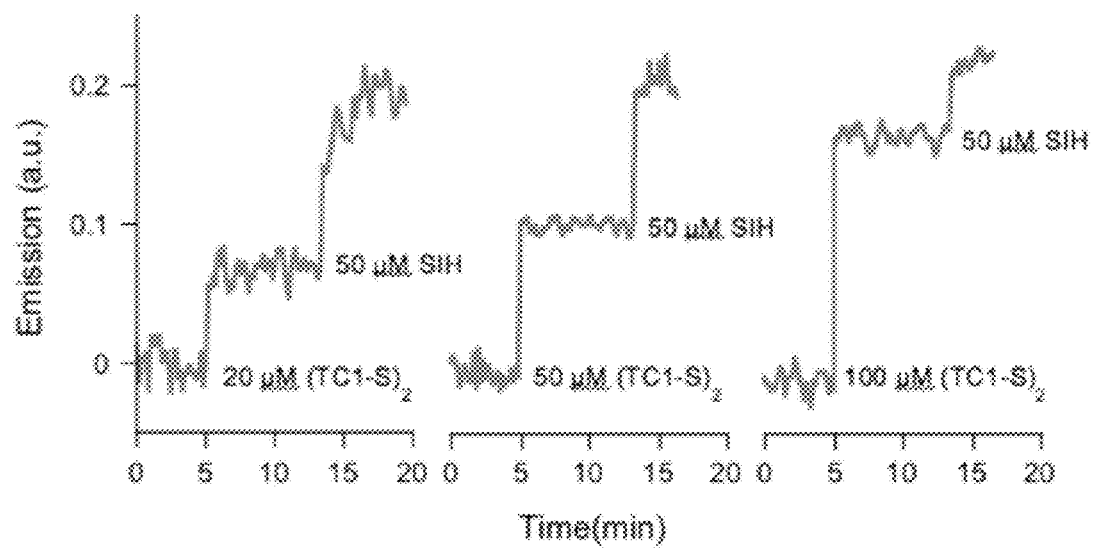

In a suspension of cultured Jurkat cells (T1B-152, acute T-cell leukemia) loaded with calcein, addition of pro-chelator (TC1-S)$_2$ caused concentration-dependent increase in fluorescence intensity (FIG. 5), thus indicating partial displacement of paramagnetic ions from calcein and consequent restoration of emission. Subsequent addition of cell-permeable high-affinity chelator SIH further increased fluorescence intensity. Because the prochelator does not coordinate iron ions, these experiments are consistent with reduction of (TC1-S)$_2$ to the thiol TC1-SH, which then engages in intracellular iron binding.

The intracellular formation of a low-spin Fe(III) complex upon exposure of Jurkat cells to (TC1-S)$_2$ was also investigated by EPR spectroscopic studies.

Figure 6:
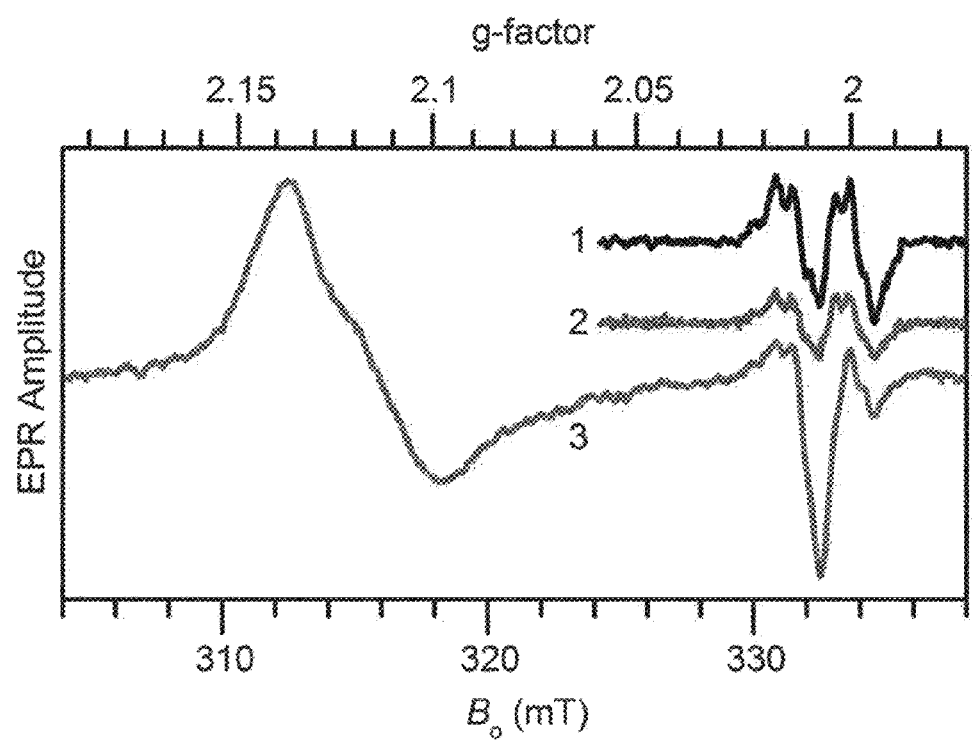

EPR data were also used to examine the effect of chelation system on the tyrosyl radical that characterizes the active site of ribonucleotide reductase (RNR), the iron-dependent enzyme that is believed to be essential in DNA biosynthesis. The spectroscopic signature of the tyrosyl radical, a doublet a g≈2, can be observed in whole-cell samples by EPR (FIG. 6, Jurkat cells, untreated sample) and intracellular iron chelation has been previously correlated with a decrease in the amplitude of this signal and hence of RNR activity. Incubation of Jurkat cells with siderophore DFO (50 μM, 3 h) resulted in loss of signal. Incubation of suspended cells with (TC1-S)$_2$ (50 μM, 1 h) also caused a decrease in RNR signal amplitude and the signal corresponding to the low-spin Fe(III) complex was recorded.

Using two different spectroscopic techniques, the experiments described herein confirmed the reduction/activation of (TC1-S)$_2$ as well as the intracellular formation of a low-spin Fe(III) complex. The disulfide, which does not coordinate iron ions, behaves as a pro-chelator and leads to intracellular iron sequestration upon its reduction to thiol TC1-SH. It was also observed that one of the intracellular effects of (TC1-S)$_2$ exposure in Jurkat cells is the reduced activity of RNR.

It is believed that the toxicity of several thiosemicarbazone-based chelators is associated with oxidative damage caused by their metal complexes, which engage in intracellular redox cycling of the Fe(III)/Fe(II) couple and concomitant generation of reactive oxygen species (ROS) through Fenton-type chemistry. Thiosemicarbazones of the invention, such as TC1-SH, however, strongly stabilizes iron in its trivalent oxidation state and, as observed for other iron scavengers including DFO, readily leads to the formation of the oxidized Fe(III) complex upon binding of Fe(II) ions. As such, thiosemicarbazones of the invention significantly reduce or even prevent iron ions from redox cycling, and hence from participating in ROS generation. This was observed by the present inventors both in vitro and in live cultured cells.

Figure 7:
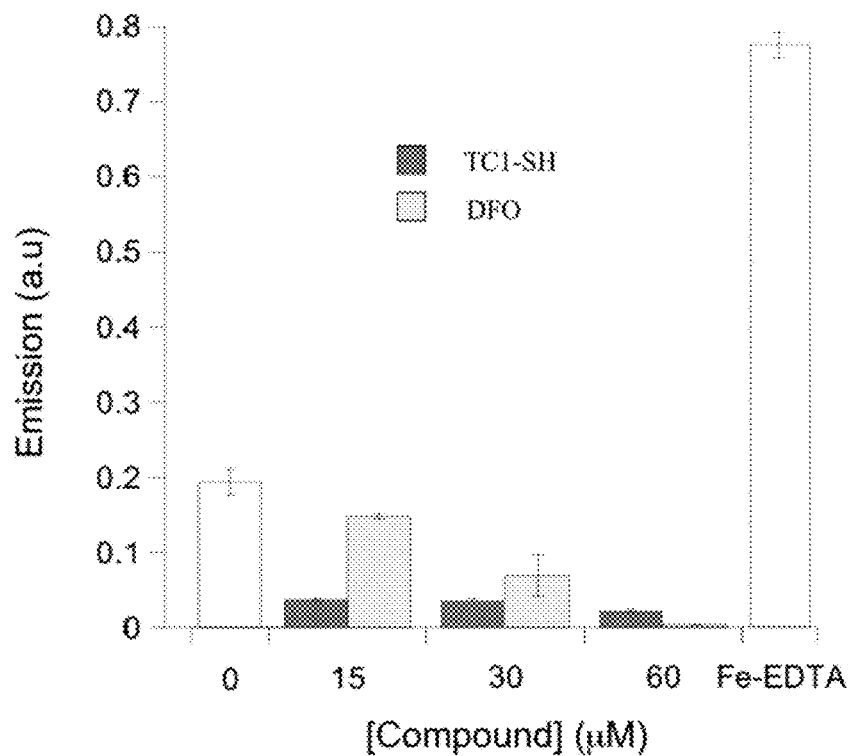

The redox activity of the iron complex(es) of thiosemicarbazones of the invention was first investigated in vitro through the benzoate hydroxylation assay, which monitors the hydroxylation of non-fluorescent benzoate ions to fluorescent salicylates in the presence of Fe(II) ions and H$_2$O$_2$. Because complexation alters that Fe(III)/Fe(II) reduction potential, iron-coordinating ligands can enhance or diminish the extent of benzoate hydroxylation when compared to the aqueous Fe(II)/H$_2$O$_2$ system. In addition, ligands and complexes can act as scavengers of ROS and interfere with benzoate hydroxylation. EDTA, which facilitates Fenton-type reactivity, was selected as a positive control; conversely, DFO was employed as an established negative control in this assay. Similar to the latter, chelator thiosemicarbazones of the invention decreased the Fenton redox activity of the Fe(II)/H$_2$O$_2$ system as indicated by the lower levels of salicylate fluorescence intensity. FIG. 7.

Figure 8:
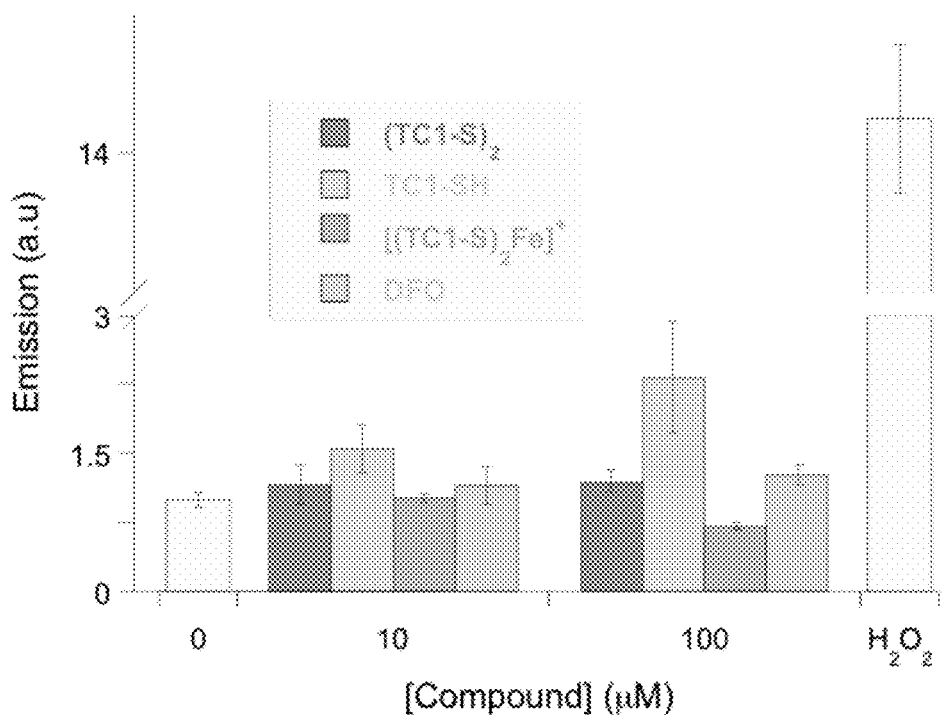

The in-vitro results above were confirmed in cultures of MBA-MD-231 breast carcinoma cells using a fluorescence-based assay of ROS generation. Added to the growth media, cell-permeable dihydrodichlorofluorescein diacetate (DCFH$_2$-DA) was hydrolized intracellularly to trap the probe dihydrodichlorofluorescein (DCFH$_2$), which was oxidized by several ROS to give the bright fluorescent product dichlorofluorescein. It is believed that DCFH$_2$ does not react directly with H$_2$O$_2$ and an excess of this species is commonly used to produce metal-mediated generation of ROS as a positive control in cell-based assays. As in the iron-mediated benzoate hydroxylation assay (FIG. 7), both disulfide prochelator (TC1-S)$_2$ and thiol TC1-SH did not elicit significant turn-on response of the fluorescent probe when compared to the positive control. FIG. 8.

In addition, some cells were treated with the preformed and isolated iron complex [(TC1-S)$_2$Fe][BF$_4$] and no generation of ROS was detected. Consistent with the formation of a redox-inactive complex, the Fe(III) species [(TC1-S)$_2$Fe][BF$_4$] was found to present low cytotoxicity in MDA-MB231 and SK-N-MC human cells, with IC$_{50}$ values greater than 30 µM in MTT viability assays in both cell lines.

These data on redox chemistry in vitro and in live cell cultures indicate that the (TC1-S)$_2$/TC1-SH chelation system does not lead to the formation of ROS and excludes iron ions from redox reactivity in simulated biological conditions.

One particular aspect of the invention provides a method for treating cancer in a subject in need of such a treatment. In particular, methods of the invention include administering to the subject a therapeutically effective amount of a redox-activated chelator, prodrug or a pharmaceutically acceptable salt thereof. The redox-activated pro-chelator is configured to be reduced, typically selectively, within a cancer cell to produce an iron ion chelating moiety whereby chelation of iron ion by the iron ion chelating moiety within the cancer cell prevents proliferation of cancer cells or causes apoptosis of cancer cells.

In some embodiments, the iron ion chelating moiety comprises thiosemicarbazone moiety.

Yet in other embodiments, the redox-activated chelator comprises a disulfide linkage that is configured to be reduced within a cancer cell to produce a thiol compound. The resulting thiol compound is configured to chelate iron ion within the cancer cell.

In one particular embodiment, the redox-activated pro-chelator is of the formula:

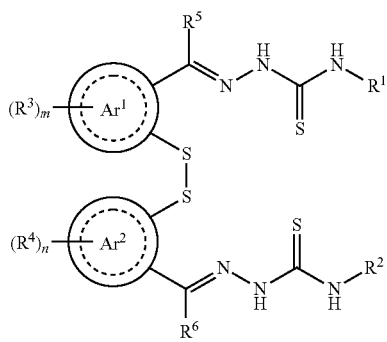

I wherein
  each of m and n is an integer from 0 to 4;
  each of Ar$^1$ and Ar$^2$ is independently aryl or heteroaryl;
  each of R$^1$, R$^2$, R$^5$ and R$^6$ is independently hydrogen, alkyl, aryl, electron withdrawing group or an anion stabilizing group;
  each of R$^3$ and R$^4$ is independently alkyl, halide, or other electron withdrawing group or an anion stabilizing group.

In some instances, m and n are 0.

Still in other instances, each of R$^1$ and R$^2$ is independently hydrogen, methyl or phenyl.

Yet in other instances, each of Ar$^1$ and Ar$^2$ is independently phenyl or pyridyl.

Typically, the disulfide group and the thiosemicarbazone moiety are substituted in ortho-position relative to one another.

In one particular embodiment, the redox-activated pro-chelator is of the formula:

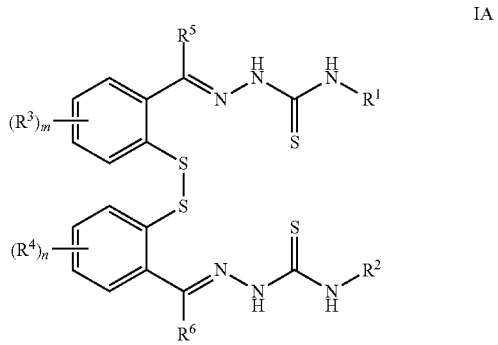

IA where m, n, R$^1$, R$^2$, R$^3$, R$^4$, R$^5$ and R$^6$ are those defined herein.

Compounds of the invention can be made by a variety of methods depicted in the illustrative synthetic reactions described below and/or in the Examples section. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "*Protective Groups in Organic Synthesis*" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Administration and Pharmaceutical Composition

The present invention includes pharmaceutical compositions comprising at least one compound of the invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Typically, compounds of the invention are administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. Typical manner of administration is generally oral using a convenient daily dosage regimen which can be adjusted according to the degree of affliction.

A compound or compounds of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention can be formulated in a wide variety of oral administration dosage forms. The pharmaceutical compositions and dosage forms can comprise a compound or compounds of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The compounds of the invention can also be formulated for parenteral administration (e.g., by injection, for example bolus injection or continuous infusion) and can be presented in unit dose form in ampoules, pre-filled syringes, small volume infusion or in multidose containers with an added preservative. The compositions can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention can be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention can also be formulated for vaginal administration. Pessaries, tampons, creams, gels, pastes, foams or sprays containing in addition to the active ingredient such carriers as are known in the art to be appropriate.

The compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compounds of the invention can be formulated for aerosol administration, particularly to the respiratory tract and including intranasal administration. The compound will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively the active ingredients can be provided in a form of a dry powder, for example, a powder mix of the compound in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compounds of the invention can be formulated in transdermal or subcutaneous drug delivery devices. These delivery systems are advantageous when sustained release of the compound is necessary or desired and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a compound of Formula (I), as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of compounds of Formula (I) or pharmaceutically acceptable salts thereof or a prodrug thereof, and one or more pharmaceutically acceptable carriers, diluents, or excipients. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of Formula (I), or a pharmaceutically acceptable salt thereof or a prodrug thereof, with one or more pharmaceutically acceptable carriers, diluents, or excipients.

When the compositions of this disclosure comprise a combination of a compound of the present disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

In one particular embodiment, redox-activated chelators comprise a thiosemicarbazone binding moiety. Known for their antibacterial, antiviral, and antifungal activity, thiosemicarbazones have been investigated as antineoplastic agents for more than five decades. Iron chelation is a useful aspect of the antiproliferative activity of these compounds, and the α-pyridine thiosemicarbazone 3-AP (Triapine) has been investigated in several clinical trials as an anticancer agent.

Based on numerous biologically active thiosemicarbazones presenting O,N,S and N,N,S donor sets, the present inventors have examined chelators of S,N,S donor sets featuring a sulfidryl group in the double role of redox switch and iron-coordinating moiety.

Some aspects of the invention include an iron ion chelator that can be selectively activated within cancer cells. As used herein, the terms "preferentially activated" and "preferentially reduced" when referring to a redox-activated chelator of the invention refers to redox-activated chelators that are reduced more easily within a cancer cell relative to a normal cell or in blood plasma. Typically, the redox-activated chelator is reduced within a cancer cell at least 50% more, typically at least 75% more and often at least 80% more than in blood plasma and extracellular space. In particular, the preferential reduction within a cancer cell can be achieved by designing the reduction potential of the redox-activated chelator to be within the reduction potential of a cancer cell. A redox-activated pro-chelator of appropriate reduction potential can be reduced within a cancer cell at least 50% more than in normal cells and tissues. Such redox-activated pro-chelator can be readily designed and produced by one skilled in the art having read the present disclosure.

Figure 9:
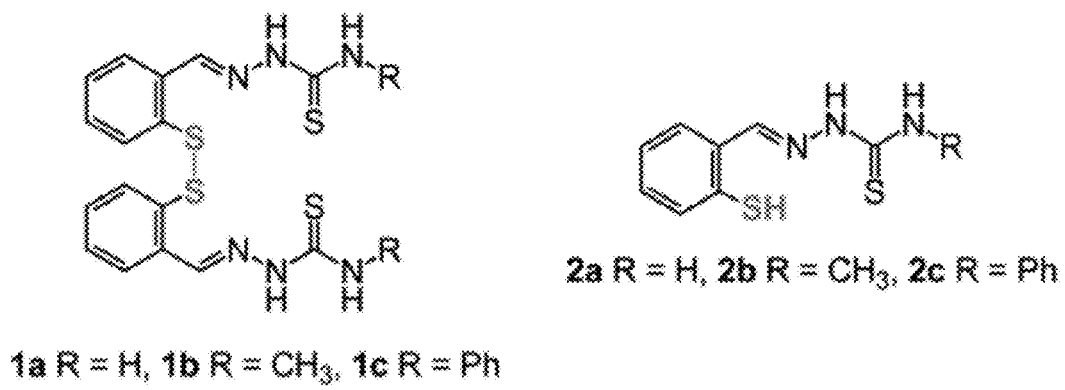
FIG. 9 shows some of the representative compounds of the invention, where compounds 1a-c are disulfide prochelators and compounds 2a-c are the corresponding thiol-containing thiosemicarbazone chelators.

In one particular embodiment, using reduction/activation strategy design, the present inventors have introduced or utilized a disulfide bond as masking group in pro-chelators of Formula 1a-c. The disulfide bond can be selectively reduced in cancer cells to thiol-containing chelators of Formula 2a-c. FIG. 9. The reversible disulfide/thiol switch (i.e., activator) can be used in intracellular equilibration with the glutathione redox buffering system, a primary indicator of the cellular redox environment. In addition, positioning of the sulfidryl group on an aromatic ring connected to the π-system of the chelating unit offers the opportunity to tune the disulfide reduction potential based on substituents of the thiosemicarbazone moiety (e.g., R=H, methyl, phenyl in 1a-c) as well as substituents on the phenyl ring itself (not shown).

Disulfide compounds 1a-c (i.e., redox-activated pro-chelators) were prepared in good yields by condensation of 2,2'-dithiodibenzaldehyde with the appropriate thiosemicarbazides. Reduction of the isolated thiosemicarbazones with dithiothreitol (DTT) afforded thiol-containing activated chelators 2a-c in quantitative yields.

Figure 10:
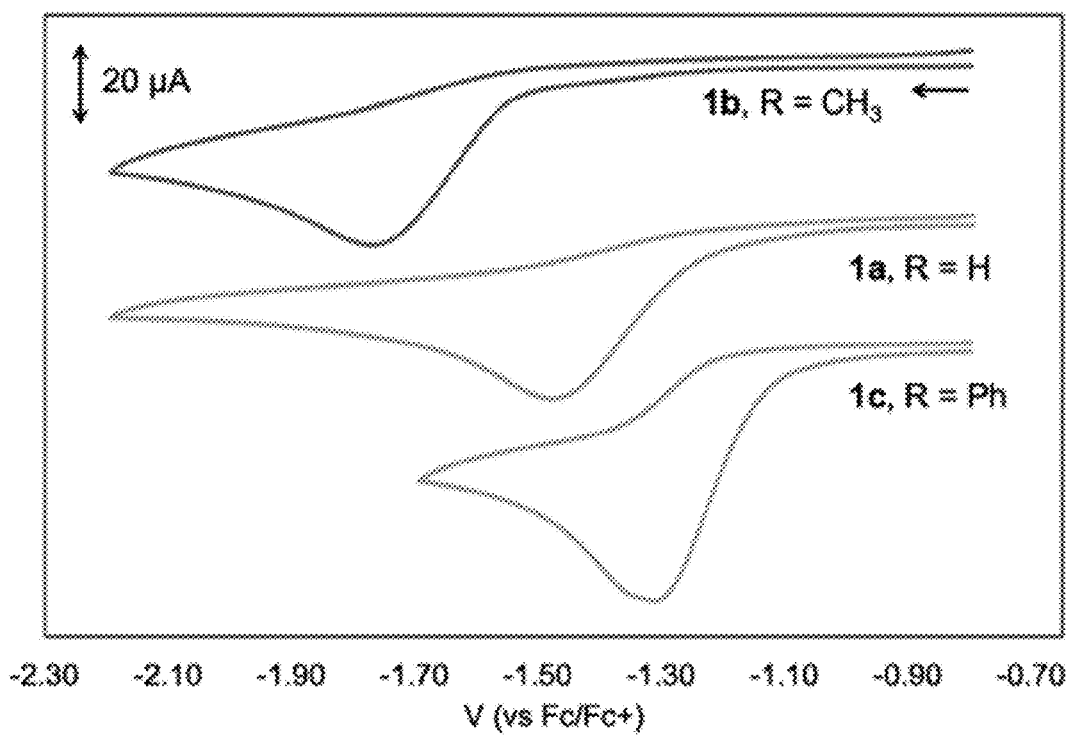
FIG. 10 is a cyclic voltammograms of disulfides 1a-c at a glassy carbon electrode in DMF with $(n-Bu_4N)(PF_6)$ as supporting electrolyte. Data collected at a 100 $mVS^{-1}$ sweep rate using $Ag/AgNO_3$ reference electrode and a platinum wire auxiliary electrode.

The reduction of disulfides 1a-c was investigated by electrochemical methods in N,N-dimethylformamide. FIG. 10. The collected cyclic voltammograms present irreversible cathodic peaks that are characteristic of aromatic disulfide reduction and correspond to the two-electron reductive process leading to formation of two thiolate ions. Consistent with reported electronic effects of substituents in aromatic disulfides, peak reduction potentials of compounds 1a-c vary considerably with the substitution on the thiosemicarbazone unit. In particular, disulfide 1c, featuring the electron-withdrawing phenyl group, is easier to reduce compared to analogues 1a and 1b. These experiments established that electronic effects of the partially conjugated chelating units modulate the thermodynamic drive to reduction of disulfide constructs. Similarly, it is expected that an electron withdrawing group substituent on the phenyl ring itself (e.g., $R^3$ and/or $R^4$ in Formula I) will also result in lower reduction potential. As used herein, the term "electron withdrawing group" refers to any substituent that draws electron density away from a given center (e.g., disulfide or thiol group in compounds 1a-c and 2a-c, respectively). Exemplary electron withdrawing group include, but are not limited to: halogens such as (F, Cl, Br, and I), nitrile (—CN), carbonyls (e.g., esters, amides, ketones, aldehydes, etc.), nitro groups ($NO_2$), and any other functional group that stabilizes an anion (e.g., the thiolate anion of compounds 2a-c).

Combination of disulfides 1a-c with an equimolar amount of Fe($BF_4$)$_2$·6$H_2O$ did not lead to formation of isolable iron complexes in organic solvents and did not elicit observable changes in the UV-visible absorption spectra of 1a-c in buffered aqueous solutions. Consistent with the modest coordinating ability of disulfide linkages in general and the conformational restraints they impose on the joint thiosemicarbazone units in this case, disulfides 1a-c behave as masked pro-chelators of low iron coordinating ability.

Conversely, thiols 2a-c react readily with Fe($BF_4$)$_2$·6$H_2O$ in organic solvents and in buffered aqueous solutions. From reactions in THF, iron complexes 3a-c were isolated by crystallization and characterized by high-resolution mass spectrometry and elemental analysis. Complexes 3a (FIG. 11) and 3b were also characterized by single crystal X-ray diffraction analysis.

As expected for tridentate thiosemicarbazone ligands, the complexes present 2:1 ligand-to-metal stoichiometry with the iron center in a distorted octahedral geometry. Without being bound by any theory, it is believed that delocalization of the electronic π-system enforces planarity of each tridentate chelating unit and therefore meridional coordination. Each iron complex is found to be a monocationic species with a $BF_4^-$ counterion. As such, the identity of the metal center is assigned as Fe(III) with each ligand acting as a monoanionic tridentate chelator.

The oxidation state of the iron center was confirmed in solution by magnetic susceptibility measurements using the Evans method. Effective magnetic moments in the 1.7-1.9$\mu_B$ range for isolated complexes 3a-c also indicated a low-spin electron configuration for the $d^5$ metal center in the ligand field of two S,N,S donor sets. The crystallographic iron-thiolate bond lengths found in complexes 3a and 3b (Fe—S1, 2.2037(9) to 2.2063(7) Å) compare well with those of other low-spin Fe(III) complexes of aromatic thiolates. Similarly, the iron-imine distances (Fe—N1, 1.9285(19) to 1.937(3) Å) are in agreement with bond lengths in low-spin Fe(III) complexes of Schiff base ligands. In addition, the bond lengths along the thiosemicarbazone chelating unit, for instance C8-S2 (1.687(2)-1.691(3) Å) and C8-N2 (1.325(4)-1.348(3) Å), compare well with those of free thiosemicarbazone ligands, thus indicating that sulfur S2 coordinates as a neutral donor (FIG. 3).

Efforts to isolate Fe(II) complexes of the thiol-containing chelators 2a-c under an inert atmosphere yielded the previously described Fe(III) complexes 3a-c, thus indicating a marked tendency of the ligands to stabilize iron in the trivalent oxidation state even in the presence of minimal amounts of adventitious air. Achieving concurrent coordination and oxidation of Fe(II) ions to form stable Fe(III) complexes, chelators 2a-c are thus reminiscent of several biological siderophores, including DFO, which therefore limit intracellular redox reactivity of the iron centers.

Cyclic voltammograms of complexes 3a-c in DMF present irreversible cathodic waves at markedly negative potentials (lower than −1.6 V relative to the ferrocene/ferrocenium couple), which are assigned to the Fe(III)/Fe(II)

couple. Insufficient solubility prevented electrochemical recordings in buffered aqueous solutions for direct comparison with Fe(III)-siderophore complexes. Nevertheless, the lack of reversibility in certain conditions (typically in a pH-dependent fashion) and especially the negative peak potentials are characteristic of DFO and other siderophores that exclusively stabilize trivalent iron centers. Conversely, numerous α-N-heterocycle thiosemicarbazones present higher reduction potentials that allow for redox cycling in the intracellular milieu; as such, the ability to produce radical species and cause oxidative damage is believed to be an important aspect of their cytotoxicity. In the case of 3-AP (i.e., 3-Aminopyridine-2-carboxaldehyde thiosemicarbazone), several clinical trials were terminated owing to adverse side effects including methemoglobinemia, a condition associated with the oxidation of blood hemoglobin.

The present inventors have also investigated the antiproliferative activity of series of pro-chelators and chelators of the invention towards human cell lines. MTT assays of cell viability (Table 1) were performed on two cancer cell lines, neuroepithelioma SK-N-MC and breast adenocarcinoma MDA-MB-231, which are well studied in the context of iron deprivation. The established antiproliferative iron chelator DFO was used as a control and its toxicity profiles compared well to literature ones for these cell lines. Viability measurements were conducted in the presence of human holotransferrin in order to load intracellular iron pools and assess antiproliferative activity related to intracellular iron deprivation.

TABLE 1

Antiproliferative activity of pro-chelators and chelators in SK-N-MC (neuroepithelioma), MDA-MB-231 (breast adenocarcinoma) and MRC-5 (normal lung fibroblast) cell cultures

| Compound | IC$_{50}$ (µM) | | |
|---|---|---|---|
| | SK-N-MC$^a$ | MDA-MB-231$^a$ | MRC-5$^b$ |
| DFO | 10.02 ± 0.06 | 17.05 ± 0.05 | 8.04 ± 0.03 |
| 1a | 8.91 ± 0.09 | 22.07 ± 0.04 | n.d. |
| 1b | 12.33 ± 0.03 | 11.92 ± 0.05 | n.d. |
| 1c | 6.81 ± 0.17 | 4.59 ± 0.06 | 30.91 ± 0.02 |
| 2a | >30 | >30 | n.d. |
| 2b | 22.53 ± 0.07 | >30 | n.d. |
| 2c | 5.19 ± 0.17 | 15.01 ± 0.05 | 15.08 ± 0.02 |

IC$_{50}$ values from MTT assays after exposure to tested compounds for $^a$48 h or $^b$72 h;
n.d.: not determined.

IC$_{50}$ values for all disulfide pro-chelators 1a-c compared well with those of DFO in both cancer cell lines. Some correlation was observed between the reduction peak potentials in FIG. 2 and the toxicity parameters, with compound 1c, which is expected to undergo more facile reduction/activation, having a higher antiproliferative activity in both cases. Furthermore, comparative study was conducted between the biological activity of disulfides 1a-c to their corresponding thiols, in which the sulfidryl group is not protected from extracellular coordination and/or redox reactivity. Notably, disulfides 1a-c present similar or significantly higher cytotoxicity compared to corresponding thiols 2a-c.

The phenyl-substituted compounds 1c and 2c, which displayed the best cytotoxicity profile in both cancer cell lines, was also evaluated in normal MRC-5 lung fibroblasts. Because normal cells divide at a lower rate, MTT assays were performed after exposures of 48 h and also 72 h (Table 1). In contrast to the observations in cancer cells, and consistent with a less reducing intracellular environment in normal tissue proliferating at a lower rate, the disulfide pro-chelator 1c was significantly less toxic than its corresponding thiol 2c in normal cells.

Conclusion

A disulfide bond was introduced within the tridentate coordination donor set of established thiosemicarbazone iron chelators. The resulting disulfide thiosemicarbazones behave as pro-chelators of low coordinating ability. Conversely, following reduction, the corresponding thiols promptly stabilize iron ions in low-spin Fe(III) complexes. The antiproliferative activities of disulfide pro-chelators in SK-N-MC (neuroepithelioma) and MDA-MB-231 (breast adenocarcinoma) cell lines compare well to those of the antiproliferative Fe(III)-chelator DFO. Notably, disulfide 1c displays higher or similar antiproliferative activity when compared to the corresponding chelator 2c in cancer cells, but presents lower toxicity than 2c in normal cells. Taken collectively, these findings are consistent with a disulfide reduction/activation that is dependent on the intracellular redox environment.

In summary, with the reported disulfide-based pro-chelator systems of the thiosemicarbazone family, the present inventors herein have illustrated the design of redox-directed iron chelation, a strategy that can lead to more selective therapeutic approaches targeting the altered iron metabolism and redox environment of cancer cells.

Example 2

(TC1-S)$_2$, TC1-SH, [(TC1-S)$_2$Fe][BF$_4$] and salicylaldehyde isonicotinoyl hydrazone (SIH) were prepared and stock solutions were freshly prepared in DMSO. Desferrioxamine mesylate salt (Aldrich) and human holo-transferrin (Aldrich) were obtained commercially and used as received. Stock solutions of Calcein-AM (AnaSpec) and DCFH$_2$-DA (Invitrogen) were prepared in DMSO, aliquoted in single-use doses and stored at −20° C. All other chemicals were purchased from common commercial sources and used without further purification.

UV-visible absorption spectra were obtained on am Agilent 8453 spectrophotometer. Fluorescence measurements were conducted on a Thermo Spectronic Aminco Bowman Series 2 Liminescence Spectrometer. Absorption and fluorescence assays in 96-well plates were recorded on a BioTek Synergy™ 2 microplate reader at the indicated wavelengths.

Cell Culture and Cell-Based Assays

MDA-MB-231 (ATCC® HTB-26™) breast adenocarcinoma cells and SK-N-MC (ATCC® HTB-10™) neuroepithelioma cells were cultured under a 5% CO$_2$ humidified atmosphere at 37° C. in Eagle's Minimal Essential Medium (EMEM) supplemented with 10% fetal bovine serum (FBS), glutamine (2 mM), sodium pyruvate (1 mM), sodium bicarbonate (1.5 mg/L), penicillin (100 units/mL), streptomycin (100 µg/mL) and 1.25 µM (1 mg/10 mL) human holo-transferrin (Aldrich) prior to use. Jurkat T lymphocytes (ATCC® T1B-152™) were cultured at 37° C. under a 5% CO$_2$ humidified atmosphere in RPMI 1640 media supplemented with 10% FBS, penicillin (5 mg/ml) and streptomycin (1 mg/ml), and maintained at a density lower than 2.0×10$^6$ cells/mL.

Conclusions

The introduction of a disulfide bond in the donor set of a thiosemicarbazone moiety led to a prochelator system that can be switched on by reduction to the corresponding thiol. The experimental findings described herein indicate that such reduction/activation is operational in biological settings. In-vitro experiments in glutathione buffer show that the reduction of (TC1-S)$_2$ occurs at concentrations and half-cell potentials that are relevant to the intracellular conditions. The increased toxicity of the prochelator in response to increased intracellular thiol levels (by NAC supplementation) supports the notion of a cell-directed redox activation leading to enhanced activity.

Following reduction, chelator TC1-SH readily binds iron ions to form a low-spin Fe(III) complex. These data demonstrate that this species is formed intracellularly. Fluorescence-based assays employing prochelator (TC1-S)$_2$ indicate that the activated chelator generated upon reduction is capable of displacing iron ions from other metal-binding species (i.e., fluorescent sensor calcein in these experiments) in cultured cells. Furthermore, EPR experiments in whole Jurkat cells provided direct evidence for the formation of the low-spin Fe(III) complex ion [(TC1-S)$_2$Fe]$^+$ as documented by its distinct spectral features. EPR data also indicated that this chelation systems leads to a decrease in the signal amplitude for the tyrosyl radical of RNR, which correlates with loss of activity of this critical enzyme for DNA biosynthesis. Additionally, fluorescence-based assays both in vitro and in live cells did not indicate any significant amount of ROS generation in this chelation approach, which is characterized by the marked stabilization of a low-spin Fe(III) center.

Thus, data indicate that the antiproliferative activity of prochelator, e.g., (TC1-S)$_2$, can be attributed to the reduction to chelator TC1-SH and to the ensuing intracellular iron sequestration, but not to oxidative damage resulting from redox chemistry of the formed iron complexes. Synthetic modifications on the thiosemicarbazone scaffold can be made to alter the disulfide reduction potential as well as lipophilicity and cell permeability of the prochelators.

The present disclosure shows that the incorporation of disulfide switches in the primary coordination sphere of biological metal scavengers is a valid strategy for the design of redox-directed chelation approaches. The elevated [GSH]/[GSSG] ratios that characterize highly proliferating malignant cells compared to neighboring normal tissue could offer an environment for preferential or selective activation of these compounds.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of treating breast cancer in a subject said method comprising administering to said subject a therapeutically effective amount of a compound of the formula:

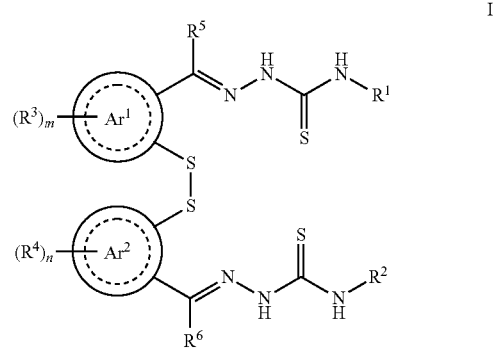

wherein
  m and n are 0;
  Ar$^1$ and Ar$^2$ are phenyl;
  each of R$^1$ and R$^2$ are independently hydrogen, methyl or phenyl; and
  R$^5$ and R$^6$ are hydrogen.

2. The method of claim 1, wherein R$^1$ is hydrogen.
3. The method of claim 1, wherein R$^1$ is methyl.
4. The method of claim 1, wherein R$^1$ is phenyl.
5. The method of claim 1, wherein R$^2$ is hydrogen.
6. The method of claim 1, wherein R$^2$ is methyl.
7. The method of claim 1, wherein R$^2$ is phenyl.

* * * * *